United States Patent
Guntzer et al.

(10) Patent No.: US 10,568,600 B2
(45) Date of Patent: Feb. 25, 2020

(54) SYSTEM AND METHOD FOR DETECTING ANATOMICAL REGIONS

(71) Applicant: GENERAL ELECTRIC COMPANY, Schenectady, NY (US)

(72) Inventors: Pierre Guntzer, Strasbourg (FR); Philippe Roy, Schiltigheim (FR); Nicolas Grussenmeyer, Bischwiller (FR); Mathieu Bedez, Colmar (FR); Yacine El Farouk, Strasbourg (FR); Gaetan Fritz, Wasselonne (FR)

(73) Assignee: General Electric Company, Schenectady, NY (US)

( * ) Notice: Subject to any disclaimer, the term of this patent is extended or adjusted under 35 U.S.C. 154(b) by 88 days.

(21) Appl. No.: 15/885,088

(22) Filed: Jan. 31, 2018

(65) Prior Publication Data

US 2019/0231294 A1 Aug. 1, 2019

(51) Int. Cl.
| | |
|---|---|
| *G06K 9/00* | (2006.01) |
| *A61B 6/00* | (2006.01) |
| *G06T 7/00* | (2017.01) |
| *G06T 7/174* | (2017.01) |
| *G06T 7/11* | (2017.01) |
| *A61B 6/03* | (2006.01) |

(52) U.S. Cl.
CPC ............ *A61B 6/5294* (2013.01); *A61B 6/488* (2013.01); *A61B 6/5217* (2013.01); *A61B 6/5229* (2013.01); *A61B 6/545* (2013.01); *A61B 6/584* (2013.01); *G06T 7/0014* (2013.01); *G06T 7/11* (2017.01); *G06T 7/174* (2017.01); *A61B 6/032* (2013.01); *A61B 6/487* (2013.01); *A61B 6/563* (2013.01); *G06T 2207/10081* (2013.01); *G06T 2207/30004* (2013.01); *G06T 2207/30204* (2013.01)

(58) Field of Classification Search
None
See application file for complete search history.

(56) References Cited

U.S. PATENT DOCUMENTS

| 8,045,771 | B2 | 10/2011 | Tao et al. |
| 9,649,079 | B1 | 5/2017 | Guntzer et al. |

(Continued)

OTHER PUBLICATIONS

McCollough et al., "Use of Water Equivalent Diameter for Calculating Patient Size and Size-Specific Dose Estimates (SSDE) in CT," The Report of AAPM Task Group 220, Sep. 2014, 23 pages.

*Primary Examiner* — Wei Wen Yang

(57) ABSTRACT

System and methods for automatically identifying anatomical regions in medical images are disclosed. A signature is computed from one or more images of a patient. The signature comprises a water equivalent diameter distribution generated from one or more images of the patient. A best matching atlas element is identified from an atlas. The atlas includes a group of atlas elements, each atlas element includes landmarks associated with a set of image data, and a signature associated with the set of image data. The signature of the best matching atlas element matches the signature of the patient the best among the atlas. Landmarks of the best matching atlas element are projected onto an image of the patient. The method can be used on its own for anatomy localization or used in conjunction with another anatomy localization method to correct the result of another method.

20 Claims, 7 Drawing Sheets

(56) References Cited

U.S. PATENT DOCUMENTS

| | | | |
|---|---|---|---|
| 2003/0007601 A1* | 1/2003 | Jaffray | A61B 6/032 378/65 |
| 2010/0303314 A1* | 12/2010 | Chen | G06T 7/33 382/128 |
| 2012/0070053 A1* | 3/2012 | Liu | G06K 9/00 382/131 |
| 2015/0305695 A1* | 10/2015 | Lahm | G16H 50/50 600/424 |
| 2017/0143291 A1 | 5/2017 | Guntzer et al. | |
| 2018/0350454 A1* | 12/2018 | Dorn | G06F 19/321 |
| 2018/0368785 A1* | 12/2018 | Wiegert | A61B 6/032 |

\* cited by examiner

SYSTEM AND METHOD FOR DETECTING ANATOMICAL REGIONS

TECHNICAL FIELD

This disclosure relates to systems and methods for automatically identifying anatomical regions (e.g., head, shoulders, chest, abdomen, pelvis, etc.) in medical images.

BACKGROUND

Various medical systems use ionizing radiation to acquire images of patients and/or provide treatment to patients, such as x-ray devices, computed tomography (CT) devices, fluoroscopic devices, and so on. For example, in a radiological imaging system, a beam of ionizing radiation (e.g., x-rays) is projected towards an exposed subject (e.g., patient). The ionizing radiation is attenuated when passing through the exposed subject and then received at a detector. The attenuation of the ionizing radiation is measured and processed to generate an image that can be viewed and analyzed.

Radiation doses can vary significantly between different types of studies, for example, a radiation dose for a routine head CT may be much lower than a dose for a multiphase abdomen and pelvis CT. In a typical CT imaging session, low dose scout images are acquired first for anatomy localization. A clinician may review the scout images, manually annotate anatomical regions, and set the radiation dose (and other scanning parameters) to acquire images of an anatomical region of interest. Or, anatomical regions can be identified automatically in the scout images without manual intervention and the local dose of radiation can be determined automatically based on some dose optimization strategies. Thus, automatic identification of anatomical regions with improved accuracy is generally desired.

SUMMARY

In one embodiment, the present disclosure provides a method for automatically identifying anatomical regions in medical images. The method comprises generating a signature of an exposed subject. The signature comprises a water equivalent diameter distribution generated from one or more images of the exposed subject. The method also comprises identifying a best matching atlas element from an atlas. The atlas includes a group of atlas elements. Each atlas element includes landmarks associated with a set of image data and a signature associated the set of image data. The signature of the best matching atlas element matches the signature of the exposed subject the best among the atlas. The method further comprises projecting landmarks of the best matching atlas element onto an image of the exposed subject to generate projected landmarks for the image of the exposed subject.

In another embodiment, the present disclosure provides a processing system for automatically identifying anatomical regions in medical images. The processing system comprises a signature generator configured to generate a signature of an exposed subject. The signature comprises a water equivalent diameter distribution generated from one or more images of the exposed subject. The processing system also comprises a signature matcher configured to identify a best matching atlas element from an atlas. The atlas includes a group of atlas elements. Each atlas element includes landmarks associated with a set of image data and a signature associated the set of image data. The signature of the best matching atlas element matches the signature of the exposed subject the best among the atlas. The processing system further comprises a landmark projector configured to project landmarks of the best matching atlas element onto an image of the exposed subject to generate projected landmarks for the image of the exposed subject.

In yet another embodiment, the present disclosure provides a non-transitory computer readable medium comprising instructions which, when executed by a processing system, cause the processing system to perform operations. The operations comprise generating a signature of an exposed subject. The signature comprises a water equivalent diameter distribution generated from one or more images of the exposed subject. The operations also comprise identifying a best matching atlas element from an atlas. The atlas includes a group of atlas elements. Each atlas element includes landmarks associated with a set of image data and a signature associated the set of image data. The signature of the best matching atlas element matches the signature of the exposed subject the best among the atlas. The operations further comprise projecting landmarks of the best matching atlas element onto an image of the exposed subject to generate projected landmarks for the image of the exposed subject.

BRIEF DESCRIPTION OF THE DRAWINGS

Various aspects of this disclosure may be better understood upon reading the following detailed description and upon reference to the drawings in which.

Figure 1:
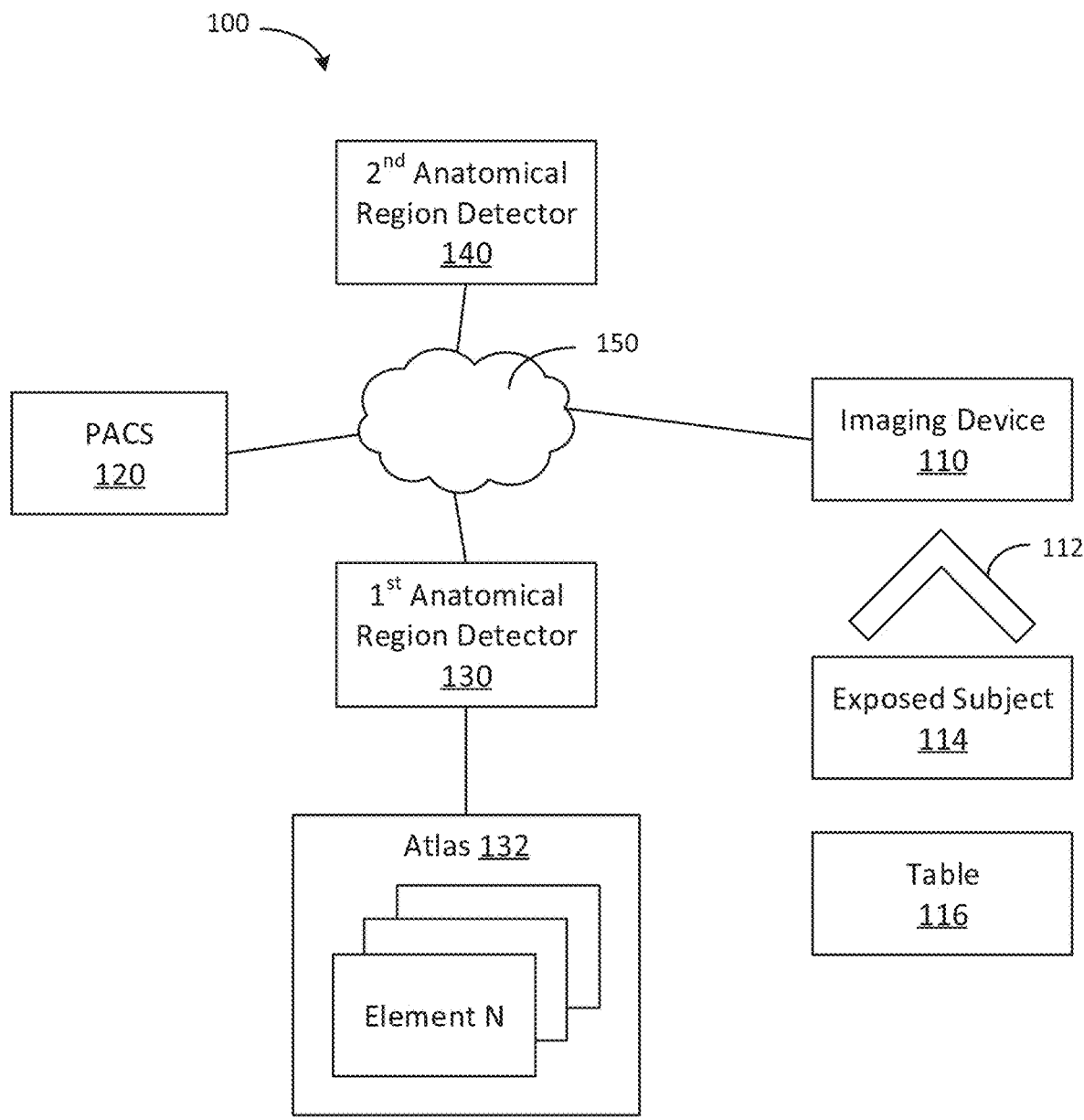
FIG. 1 is a block diagram of the environment for automatically identifying anatomical regions in medical images, in accordance with an exemplary embodiment.

The drawings illustrate specific aspects of the described systems and methods for automatically identifying anatomical regions. Together with the following description, the drawings demonstrate and explain the principles of the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

One or more specific embodiments of the present disclosure are described below in order to provide a thorough understanding. These described embodiments are only examples of systems and methods for automatically detecting anatomical regions. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Referring to the figures generally, the present disclosure is to provide systems and methods for automatically identifying anatomical regions in medical images. In some embodiments, the systems and methods disclosed herein are used in conjunction with another anatomy localization system/method to improve the accuracy of anatomy identification, for example, to remove false positives from results of the another method. In some embodiments, the disclosure is used on its own for identifying anatomical regions. An exemplary method includes generating a signature for a patient. The signature includes patient specific metrics and does not depend on the model and/or protocol used to acquire the images. For example, the signature includes a distribution of water equivalent diameter generated from one or more images of the patient. The signature may also include other patient specific metrics, such as sex, age, size, etc.

The signature of the patient is compared to the same kind of signatures of a set of atlas elements (or phantoms). An atlas includes this set of elements, each having image data and associated signature. Positions of the boarders of anatomical stages (also known as landmarks) have already been annotated for each atlas element. An atlas element for which the signature matches the signature of the patient the best is identified from the atlas. The landmarks of the identified best matching atlas element are projected onto the patient image. If the method disclosed herein is used in conjunction with another anatomy localization method, the projected landmarks on the patient image can be compared to the landmarks determined by the another method. A confidence score is given based on the comparison to each landmark identified by the another method to indicate how likely the landmark is correct. For example, if the discrepancy between a projected landmark and a corresponding landmark in the result of the another method is substantial, the confidence score associated with this landmark indicates "unlikely." The "unlikely" landmark can be removed from the results of the existing method. In some embodiments, the "unlikely" landmark can be replaced by the corresponding projected landmark. In some embodiments, if the another method fails to recognize a landmark, the projected landmark can be used to complement the result.

As discussed above, because the signature is patient specific and does not depend on the imaging device and/or protocol used to acquire the images, the disclosure does not require that the image of the patient at issue and the atlas images are produced by the same model/protocol. Conventionally, two images produced by different models/protocols are difficult to compare because the gray levels of an image highly depend upon the machine/protocol. With the patient specific signature being used for comparison, a wide set of atlas element coming from various devices can be used as atlas elements. That is to say, the disclosure works for images generated by an imaging device for which no atlas element is present in the atlas because device manufacturer or model does not affect the patient specific metrics in the signature.

Now referring to FIG. 1, a block diagram of the environment 100 for identifying anatomical regions in medical images is shown, in accordance with an exemplary embodiment. As illustrated in FIG. 1, in some embodiments, the environment 100 comprises an imaging device 110, a picture archiving and communication system (PACS) 120, a first anatomical region detector 130, and optionally a second anatomical region detector 140, connected via communication connection 150. The imaging device 110 may employ a beam of ionizing radiation 112 to acquire medical images for an exposed subject 114 resting on a table 116. The medical images may be stored in the PACS 120. The first anatomical region detector 130 may identify anatomical regions in the medical images with reference to an atlas 132. In some embodiments, the first anatomical region detector 130 works in conjunction with the second anatomical region detector 140 to correct the results of the second anatomical region detector 140.

The imaging device 110 can be an x-ray (e.g., angiographic) imaging device, CT device, fluoroscopic imaging device, or any other medical imaging device that use ionizing radiation (e.g., x-rays) to acquire images. In particular, a beam of ionizing radiation 112 is projected towards the exposed subject 114 (e.g., patient) resting on the table 116. The ionizing radiation 112 is attenuated when passing through the exposed subject 114 and then received at a detector or a photographic plate. The attenuation of the ionizing radiation 112 is measured and processed to generate an image that can be viewed and analyzed. In some embodiments, the imaging device 110 first uses low dose of radiation to perform an initial topographic scan. Slice images and one or more scout images on the exposed subject 114 can be acquired.

Figure 2:
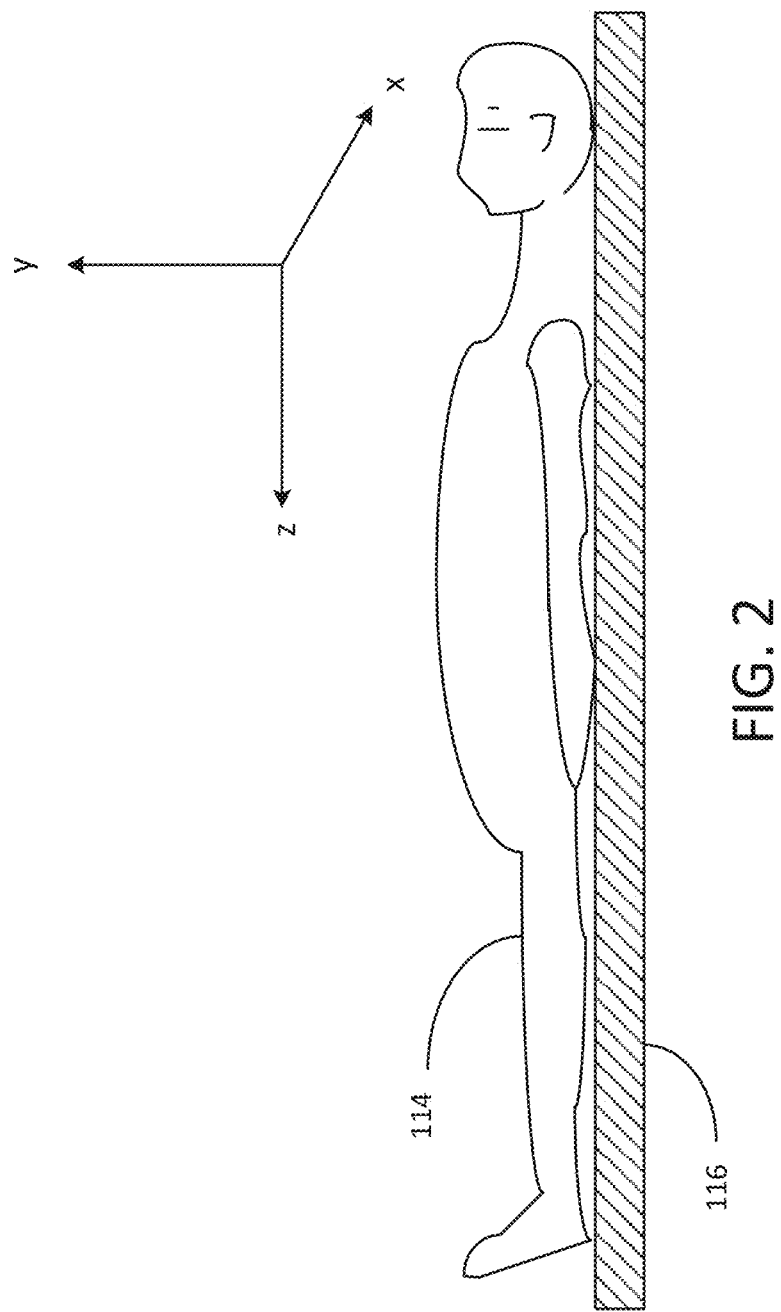
FIG. 2 is a schematic diagram illustrating the axes with respect to an exposed subject on a table, in accordance with an exemplary embodiment.

In some embodiments, a scout image is a two-dimensional image, which is a general illustration of a projected view of the exposed subject 114. In some embodiments, two scout images of the same scene are acquired under different points of view, such as a lateral (LAT) view and an anteroposterior (AP) view, which allows reconstruction of a three-dimensional outer shape of exposed subject 114. FIG. 2 shows an exemplary coordinate system that the imaging device 110 uses, to explain the LAT view and the AP view. X-axis is a horizontal axis extending in a direction from a left-hand border to a right-hand border of a surface of the table 116, y-axis is a vertical axis extending in a direction from the floor upwards in direction towards a top of the table 116, and z-axis is a longitudinal axis extending in a direction from head to toe of the exposed subject 114. The LAT view is a projected view of the exposed subject 114 in the YZ plane, and the AP view is a projected view of the exposed subject 114 in the XZ plane.

Figure 3:
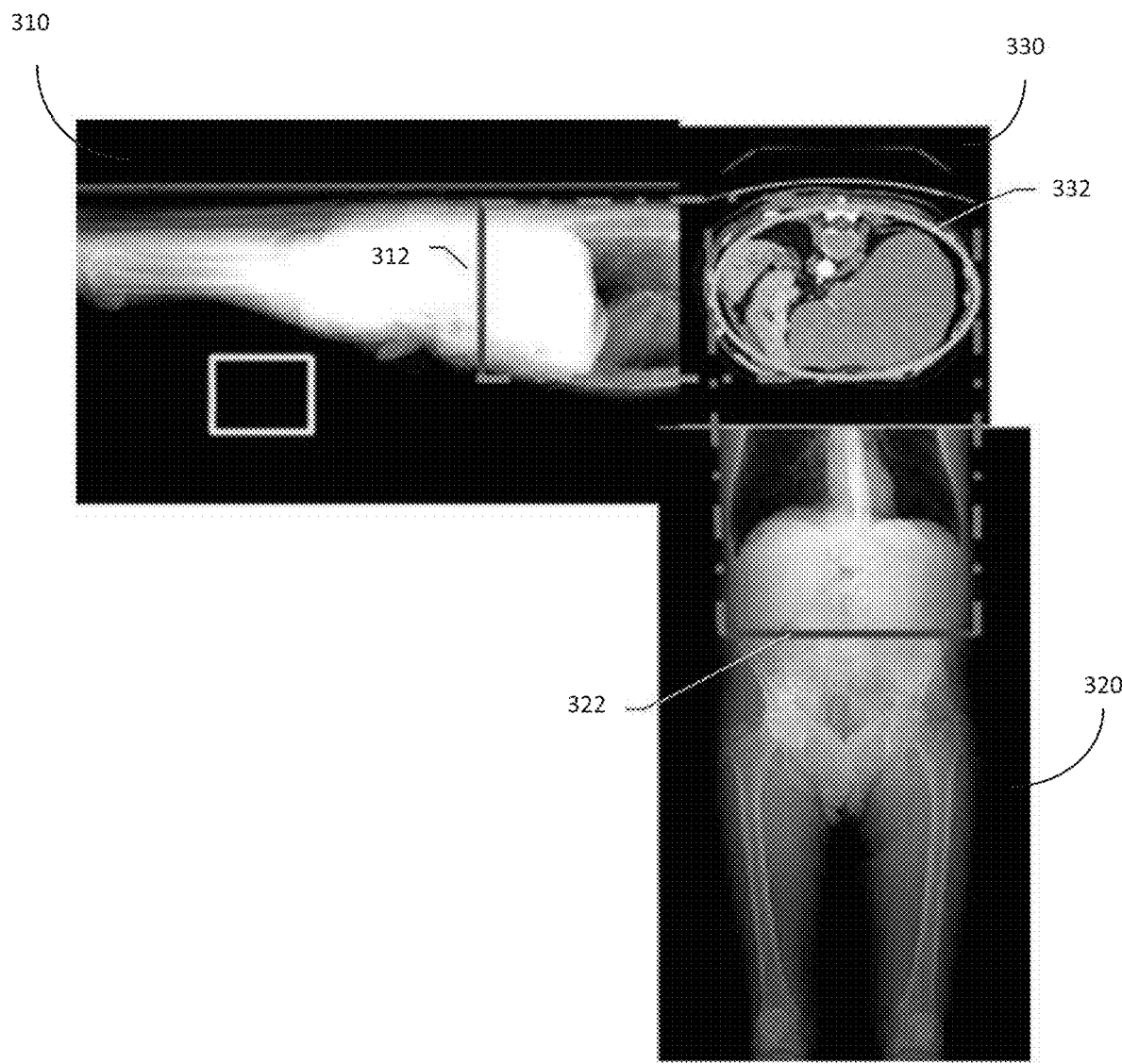
FIG. 3 shows a slice image with respect to scout images, in accordance with an exemplary embodiment.

Each horizontal line of a scout image is associated with a different section of anatomy along the z-axis of the exposed subject. FIG. 3 shows an exemplary slice image with respect to scout images. As shown in FIG. 3, a slice image 330 shows an elliptical representation 332 of the exposed subject 114 as a cross-sectional image. The elliptical representation 332 corresponds to a graphic line 312 in the LAT scout image 310 and a graphic line 322 in the AP scout image 320. In some embodiments, a user can select a region of interest from the scout images 310 and 320 by changing the positions of the graphic lines 312 and 314 and view the corresponding slice images.

In some embodiments, the imaging device 110 generates and/or stores the scout images in the Digital Imaging and Communications in Medicine (DICOM) format. Other formats can also be used, such as JPEG, TIFF, GIF, PNG, etc. In some embodiments, the scout image data includes a collection or series of tags where each tag includes pixel data having a value that represents the pixel (e.g., basic unit of programmable color on a display monitor) associated with the tag. The scout image data may also include metadata associated with patient specific metrics, such as sex, age, size, and so on.

The PACS 120 stores medical images (e.g., scout images, slice images) acquired by the imaging device 110 in a database or registry. In some embodiments, the images are stored in PACS 120 by healthcare practitioners (e.g., technicians, physicians, radiologists) after a medical imaging of a patient and/or automatically transmitted from imaging device 110 to PACS 120 for storage.

The first anatomical region detector 130 can receive images of the exposed subject 114 from the imaging device 110 and/or the PACS 120, determine a signature of the exposed subject from the images, identify an atlas element from the atlas 132 for which the signature matches the signature of the exposed subject 114 the best, and project landmarks of the best matching atlas element onto an image of the exposed subject. In some embodiments, the first anatomical region detector 130 works in conjunction with the second anatomical region detector 140 to correct the results of the second anatomical region detector 140. Structures of the first anatomical region detector 130 and the atlas element will be explained in detail below with reference to FIGS. 4 and 6.

The second anatomical region detector 140 can be any appropriate detector that uses a different method than the first detector 130 to identify anatomical regions in the scout image(s) of the exposed subject 114 received from the imaging device 110 and/or the PACS 120. In some embodiments, the second anatomical region detector 140 can rely on the first anatomical region detector 130 to correct its results of region detection. An exemplary method for identifying anatomical regions that can be used by the second detector 140 is described in U.S. patent application Ser. No. 14/510,815 (issued as U.S. Pat. No. 9,649,079, "the '079 patent"), which is incorporated herein in its entirety by reference. The method described in the patent uses an AP scout image of an exposed subject acquired by a CT device. A contour of an extremity of the exposed subject is calculated from the AP scout image, and the contour is delineated by anatomical landmarks (i.e., boarders of the anatomical stages) that mark an abrupt change in the thickness of the exposed subject. Other landmarks that might not correspond to an abrupt change in the thickness can be identified by applying heuristic and/or auxology criteria to recognize some specific shapes in the exposed subject.

Results of the method disclosed in the '079 patent may sometimes include false positives because in general, the method tries to identify a pattern in the AP scout image and returns a portion of the image that corresponds to this pattern the best. However, if the pattern is not present in the image, the method may still return a false positive. For the pelvic region identification in particular, the scout image may include a very small part of the pelvic region or may not contain the pelvic region but other shapes that look like the missing pelvis. Errors can occur in two situations. First, the method may use the maximum of an energy function to finds out the "best candidate" for the start of the pelvic region. If the pelvis is not included in the scout image, this maximum is irrelevant. Second, the method may identify a region that looks like a pelvis but is not a pelvis. In these situation, the second detector 140 can rely on the first detector 130 to remove the false positives, as will be discussed below in detail.

The communication connection 150 facilitates communication among the devices and systems shown in FIG. 1. The communication connection 150 can be implemented by any appropriate wired connection, wireless connection, or any combination therefore, such as cable, data bus, universal serial bus (USB) connection, radio frequency (RF) connection, infrared connection, optical connection, near field communication (NFC), wide area network (WAN), local area network (LAN), the Internet, a cloud-based computing infrastructure, etc.

It should be understood that the environment 100 for identifying anatomical regions as shown in FIG. 1 is for illustration, not for limitation. Any appropriate environment can include more, fewer, and/or different components. Some components can be integrated, for example, the first anatomical region detector 130 can be integrated with the second anatomical region detector 140. Variations are contemplated by this disclosure.

Figure 4:
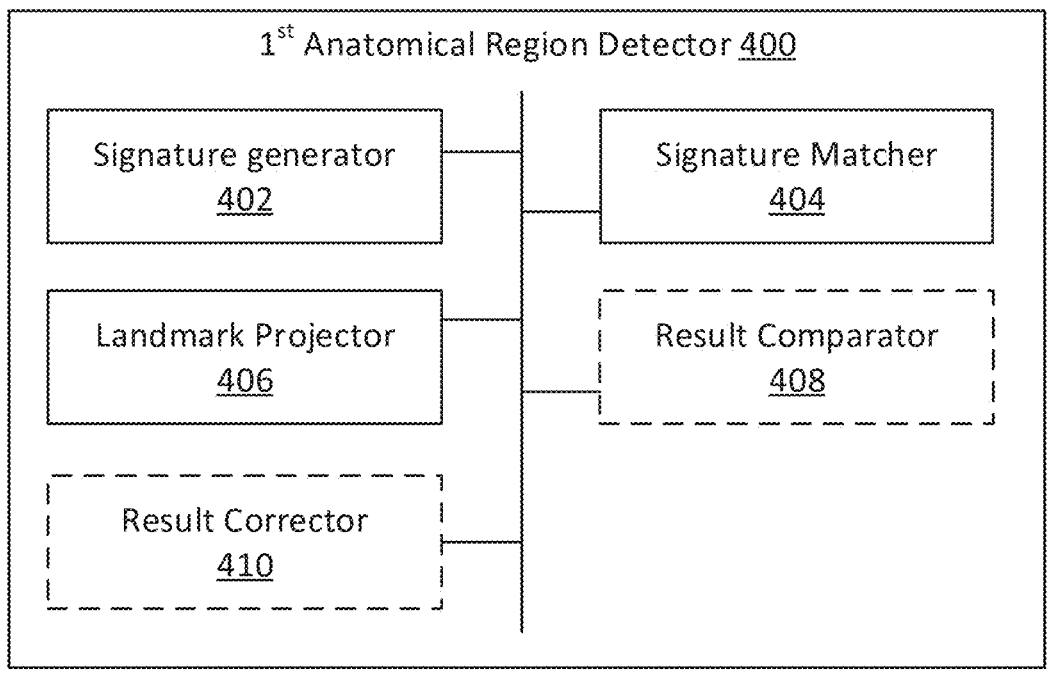
FIG. 4 is a block diagram of a first anatomical region detector which can be used in FIG. 1, in accordance with an exemplary embodiment.

Referring to FIG. 4, a block diagram the first anatomical region detector 400 is shown, in accordance with an exemplary embodiment. The first anatomical region detector 400 may be used as the first anatomical region detector 130 in FIG. 1. The first anatomical region detector 400 may be implemented on any appropriate processing system, such as system-on-a-chip system, personal computer, workstation, cloud-based computing system, and so on. In some embodiments, the first anatomical region detector 400 may be implemented on more than one processing system, i.e., a portion of the first detector 400 is run on one processing system, and another portion of the first detector 400 is run on another processing system.

As illustrated in FIG. 4, in some embodiments, the first anatomical region detector 400 comprises a signature generator 402, signature matcher 404, landmark projector 406, and optionally a result comparator 408, and result corrector 410. The signature generator 402 generates a signature of an exposed subject (e.g., patient) from one or more images of the exposed subject. The signature matcher 404 identifies an atlas element from the atlas for which the signature matches the signature of the exposed subject the best. The landmark projector 406 projects landmarks of the best matching atlas element onto an image of the exposed subject. The result comparator 408 compares the projected landmarks to the result of the second anatomical region detector 140. The result corrector 410 corrects the result of the second detector 140 based on the comparison.

The signature generator 402 generates a signature that includes a water equivalent diameter distribution from one or more images of the exposed subject. As known in the art, the x-ray attenuation of the exposed subject can be expressed in terms of a water cylinder having the same x-ray absorption. The area and diameter of such a cylinder of water are referred to as the water equivalent area ($A_w$) and water equivalent diameter ($D_w$). The water equivalent diameter distribution, as used herein, refers to the various water equivalent diameters $D_w$ along the longitudinal axis (i.e., the z-axis in FIG. 2).

Various methods may be used to calculate the water equivalent diameters $D_w$ along the longitudinal axis. For example, an article titled "Use of Water Equivalent Diameter for Calculating Patient Size and Size-Specific Dose Estimates (SSDE) in CT", *the Report of AAPM Task Group* 220, discloses a method for calculating water equivalent diameter from CT slice images. In some embodiments, the disclosure herein uses a new method for calculating water equivalent diameter distribution which is faster than the method disclosed in the article.

Figure 5:
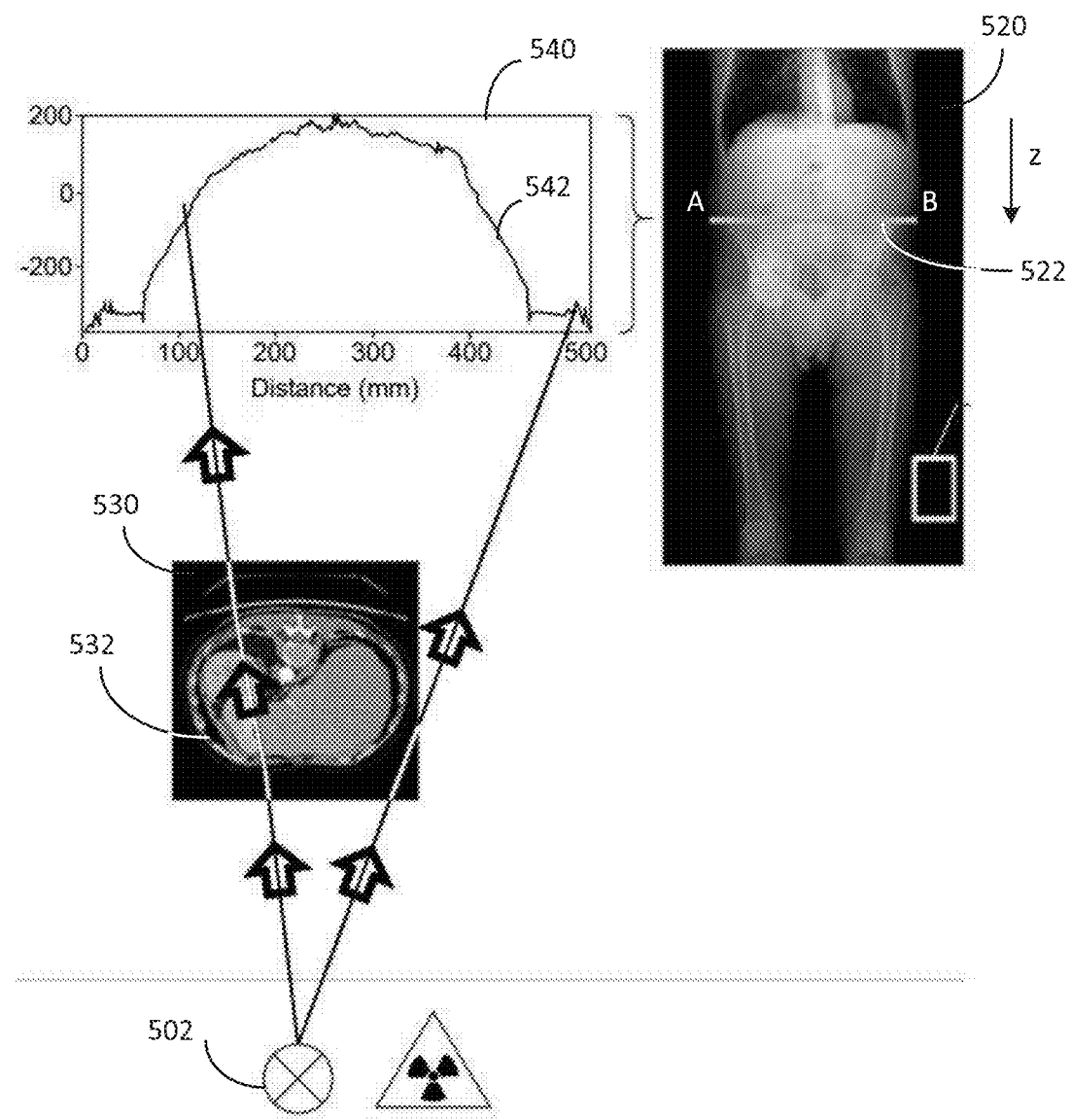
FIG. 5 illustrates calculating water equivalent diameter distribution by using the slice image and the scout image, in accordance with an exemplary embodiment.

FIG. 5 illustrates the method for fast calculating water equivalent diameter distribution, in accordance with an exemplary embodiment. The method uses a few (e.g., 3, 4, 5, etc.,) slice images 530 and one or more scout images 520. The slice images are expressed in CT numbers (i.e., normalized to the linear attenuation of water) with the unit of Hounsfield Units (HU). Water equivalent diameters are calculated from the slice images as follows:

$$D_w = 2\sqrt{A_w/\pi} = 2\sqrt{\left[\frac{1}{1000}\overline{CT(x,y)}_{ROI} + 1\right]\frac{A_{ROI}}{\pi}}, \quad (1)$$

wherein $\overline{CT(x,y)}_{ROI}$ is the mean CT number in the region of interest (ROI), and $A_{ROI}$ is the area of the ROI.

Unlike slice images, the pixel values of a scout image are not normalized to absolute units, but in grey levels, for example. As shown in FIG. 5, Each pixel (e.g., A, B) in the AP scout image 520 is associated with an x-ray path from the source 502, through the exposed subject, to the detector. The pixel value is proportional to the total attenuation along this x-ray path. An estimate of the overall water equivalent diameter at the position of line AB is proportional to the sum of the pixel values within the bound of the exposed subject. However, the relationship between the water equivalent diameter and pixel values can vary among device models/protocols. On the other hand, because a slice image is a section along the z-axis which corresponds to a line of a scout image, the relationship between the grey levels of a particular scout image and the water equivalent diameter can be calibrated by the water equivalent diameters calculated from the slice images.

For example, as shown in FIG. 5, the scout image 530 shows the location (i.e., line AB) of the slice image 520 with respect to the exposed subject 114. The water equivalent diameter $D_w$ of the slice image 530 can be calculated according to equation (1). The sum of grey levels along line AB corresponds to the calculated $D_w$. In some embodiments, water equivalent diameters calculated from a few (e.g., 3, 4, 5, etc.) slice images and grey level sums at corresponding positions of the scout image can be fit into a linear relationship. Thus, for each horizontal line of the scout image, the sum of gray levels within the boundary can be calculated and translated into water equivalent diameter using, for example, an interpolation. The water equivalent diameter distribution can be expressed as a curve. For example, a curve 542 in a graph 540 shows the water equivalent diameter distribution along the z-axis. The distribution can also be expressed in other forms, e.g., lookup table. Although FIG. 5 shows that an AP scout image 520 is used to calculate the water equivalent diameter distribution, it should be understood that a different scout image (e.g., LAT scout) can be used for the calculation. In some embodiments, more than one scout images can be used.

In some embodiments, the sum of attenuations may include contributions from voxels of the exposed subject and the surrounding media (e.g., table, air, clothes, mattress, etc.). The contribution of the exposed subject can be isolated from the surrounding media when the water equivalent diameter is calculated. An exemplary method for isolating attenuations due to the exposed subject is described in U.S. patent application Ser. No. 14/946,077 (US 2017/0143291), which is incorporated herein in its entirety by reference.

In some embodiments, the signature generator 402 may apply convolution filters (e.g., median filters, Gaussian blur filters, etc.) to the scout image data before calculating the water equivalent diameter distribution. Pre-processing the scout image can aid in determining the boundaries of the exposed subject. For example, the signature generator 402 may calculate the boundaries by comparing or analyzing a greyscale intensity of candidate pixels.

Because the water equivalent diameter distribution is a normalized measure of attenuation, it is patient specific and does not rely on the model and/or protocol used to acquire the images. In some embodiments, the signature may include other patient specific metrics besides the water equivalent diameter distribution, such as age, sex, size, etc. The signature may be a weighted combination of these metrics.

Figure 6:
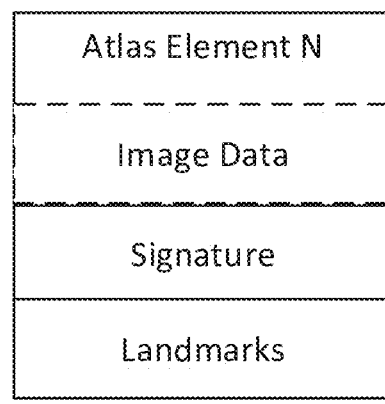
FIG. 6 is a structure of an atlas element, in accordance with an exemplary embodiment.

Referring back to FIG. 4, the signature matcher 404 identifies a best matching atlas element from the atlas 132 by comparing the signature of the exposed subject matter to the signature of each atlas element. The atlas 132 includes a set of images of the same kind (e.g., AP or LAT scout) and each particular image in the atlas is called an atlas element. FIG. 6 shows an exemplary structure of an atlas element. As shown in FIG. 6, in some embodiments, an atlas element includes a set of image data, signature associated with the set of image data, and landmarks associated with the set of image data. In some embodiments, an atlas element does not include the image data, but includes the signature and the landmarks. The signature may include the water equivalent diameter distribution (e.g., curve, lookup table) calculated for the image data, and other metadata such as age, sex, size, etc. of the subject of the image data. The landmarks annotate the positions of borders of anatomical stages (e.g., head, shoulder, chest, abdomen, pelvis, lower limb, etc.) for the image data. In some embodiments, the landmarks were annotated or corrected manually by a clinician beforehand.

In some embodiments, the atlas 132 comprises a pre-selected set of various patients. The atlas 132 may include various numbers of atlas elements (e.g., 20, 30, 50, 100, etc.). In some embodiments, the imaging device 110 used to acquire the image(s) of the exposed subject 110 may not have an atlas element present in the atlas 132. In other words, because the signature contains only patient specific metrics, atlas element from different manufacturers or models can be used.

To identify an atlas element for which the signature matches the signature of the patient image the best, a score is calculated as follows, in some embodiments:

$$\text{Score} = \Sigma_{j \in (WED\ distribution)} |WED_j(\text{atlas element}) - WED_j(\text{patient})|, \quad (2)$$

wherein $WED_j(\text{atlas element})$ is the water equivalent diameter at a line of the atlas element, and $WED_j(\text{patient})$ is the water equivalent diameter at a line of the patient image that correspond to the position of the line of the atlas element. This equation represents the line-by-line sum of the difference between the water equivalent diameter of the patient and the water equivalent diameter of the atlas element. In some embodiments, the score is computed based on partial matching between an atlas element and the patient signature. For example, the area from which the patient signature is generated might correspond to only 80% of the area of the atlas element, or vice versa. In these situations, the score may be computed for the overlapping areas. In some embodiments where the signature includes multiple metrics, the score is calculated as follows:

$$\text{Score} = \Sigma_{i \in (Signature)} \text{Weight}_i | S_i(\text{atlas element}) - S_i(\text{patient}) |, \quad (3)$$

wherein $S_i$ is a metric in the signature (i.e., water equivalent diameter distribution, age, sex, size, etc.), and $\text{Weight}_i$ is a predefined weight given to the metric. This equation represents the weighted sum of the difference of each signature component between the atlas element and the exposed subject 114.

The atlas element with the lowest score (i.e., the minimum difference) is determined to be the best match for the exposed subject 114 at issue. In some embodiments, a threshold score is set. If the lowest score of the atlas 132 is greater than the threshold score, the signature matcher 404 may determine that there is not an atlas element stored in the atlas 132 that matches or nearly matches the image of the exposed subject 114. In further embodiments, the signature matcher 404 may use a different atlas comprising a different set of atlas elements for the matching in this situation. In some embodiments, the atlas 132 may be enhanced to include more atlas elements.

Referring back to FIG. 4, the landmark projector 406 projects the landmarks of the identified besting matching atlas element onto the image of the exposed subject 114 to generate projected landmarks on the image. As discussed above, landmarks have been annotated for the atlas element. The landmark projector 406 may extract various landmarks (i.e., positions) from best matching atlas element, identify corresponding positions on the image of the exposed subject (e.g., positions of corresponding z-value), and annotate the corresponding positions.

Figure 7:
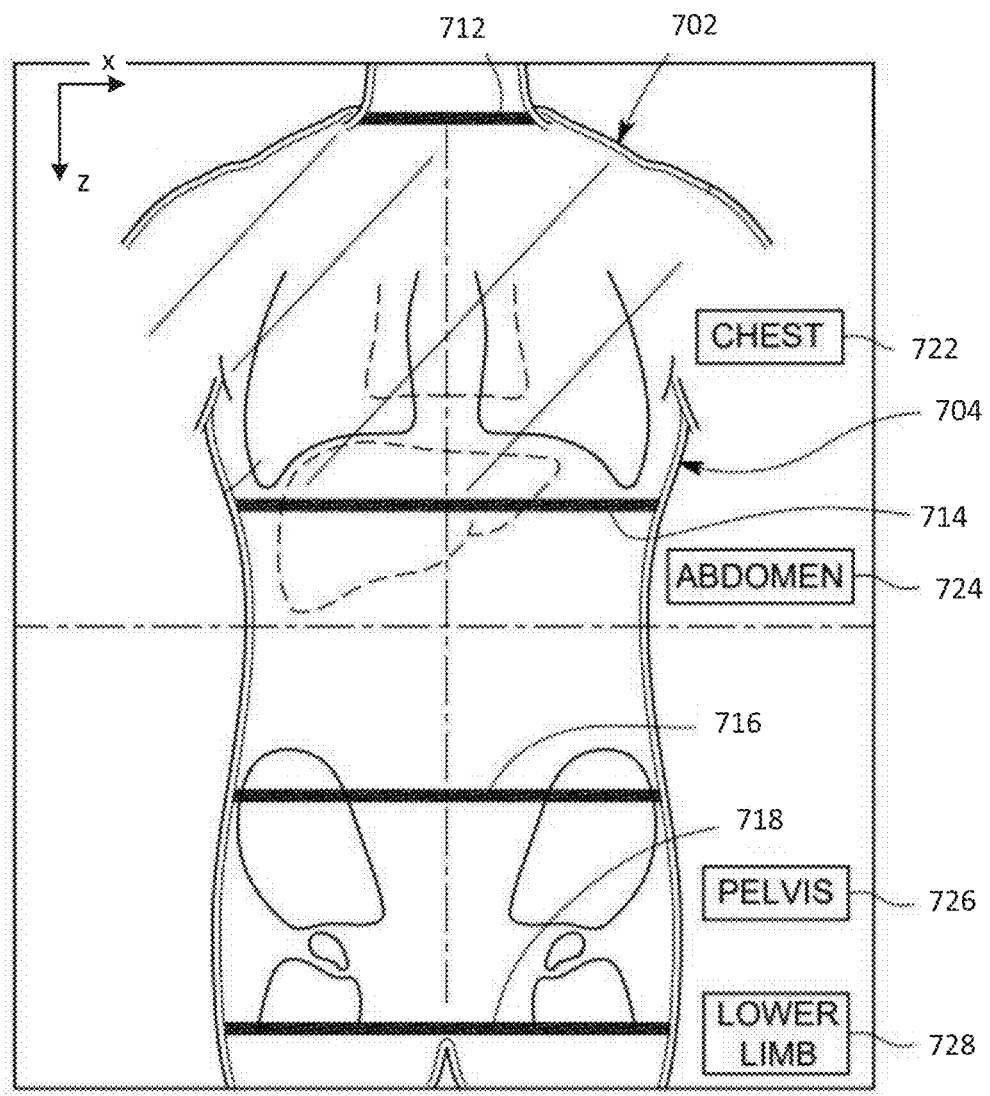
FIG. 7 illustrates landmarks on an image of a human body, in accordance with an exemplary embodiment.

FIG. 7 shows the landmarks and anatomical stages on an AP scout image of a human body, in accordance with an exemplary embodiment. The contours 702 and 704 define the boundaries of the exposed subject. Line 712 marks the start of chest 722, line 714 marks the end of chest 722 and the start of abdomen 724, line 716 marks the end of abdomen 724 and the start of pelvis 726, and line 718 marks the end of pelvis 726 and the start of lower limb 728. Lines 712, 714, 716, and 718 are landmarks that mark the positions of borders of anatomical stages 722, 724, 726, and 728. It should be understood that FIG. 7 is for illustration not for limitation. An image may not include all the landmarks but only one or some of the landmarks.

In some embodiments, the result of the first anatomical region detector 400 is used on its own for automatic anatomy localization. In some embodiments, the result of the first detector 400 is used to correct the result of the second detector 140. The first detector 400 may further comprises a result comparator 408. In some embodiments, the result comparator 408 compares the landmarks identified by the second detector 140 to the corresponding landmarks identified by the first detector 400 and gives a confidence score to each landmark based on the comparison. The confidence score indicates how likely the landmark identified by the second detector 140 is correct. For example, the result comparator 408 determines the difference in z-axis values between a landmark (e.g., landmark 712, 714, 716, or 718) determined by the landmark projector 406 and a corresponding landmark determined by the second detector 140. If the difference is substantial (i.e., the two landmarks are far away from each other), the result comparator 408 gives a low confidence score to indicate that the landmark determined by the second detector 140 is "unlikely" to be correct. If the difference is small (i.e., the two landmarks are close), the result comparator 408 give a high confidence score to indicate that the landmark determined by the second detector 140 is "likely" to be correct.

In some embodiments, the confidence score has a negative association with the difference, i.e., the greater the difference, the lower the confidence score. In some embodiments, the result comparator 408 compares the difference with a predetermined threshold. If the difference is greater than the threshold, the confidence determiner 408 gives a first confidence score. If the difference is smaller than the threshold, the confidence determiner 408 give a second confidence score, which is higher than the first confidence score. In some embodiments, if a landmark identified by the second detector 140 does not find a counterpart in the result of the landmark projector 406, the confidence determiner 408 gives a low confidence score to indicate so.

Still referring to FIG. 4, the first detector 400 may further comprise a result corrector 410 configured to correct the results of the second detector 140. For example, if the confidence score associated with a particular landmark is low (i.e., the landmark is unlikely to be correct), the result corrector 410 may remove or replace that particular landmark. In some embodiments, the result corrector 410 compares each confidence score against a predefined confidence threshold. If the confidence score is lower than the predefined confidence threshold, the result corrector 410 corrects the associated landmark. For example, if the second detector 140 identifies a landmark which does not have a counterpart in the results of the first detector 400, the result corrector 410 may remove this landmark from the results of the second detector 140. In some embodiments, if the discrepancy between a landmark identified by the second detector 140 and a corresponding landmark identified by the first detector 400 is substantial, the result corrector 410 may replace the landmark determined by the second detector 140 with the corresponding landmark determined by the first detector 400.

In further embodiments, the second detector 140 might have failed to identify a landmark that is identified by the first detector 400. For example, the first detector 400 identifies a border between the pelvis and the lower limb (e.g., landmark 728 in FIG. 7) while the second detector 140 failed to detect such a border. The result corrector 410 may add this landmark to the results of the second detector 410. Generally, it is assumed that an anatomical region in the best matching atlas element corresponds roughly to the same anatomical region in the real patient, which allows modification of the energy function used or deduction of the anatomical region not included in the patient image. The closer the atlas element matches the patient image, the more accurate correction can be achieved.

Figure 8:
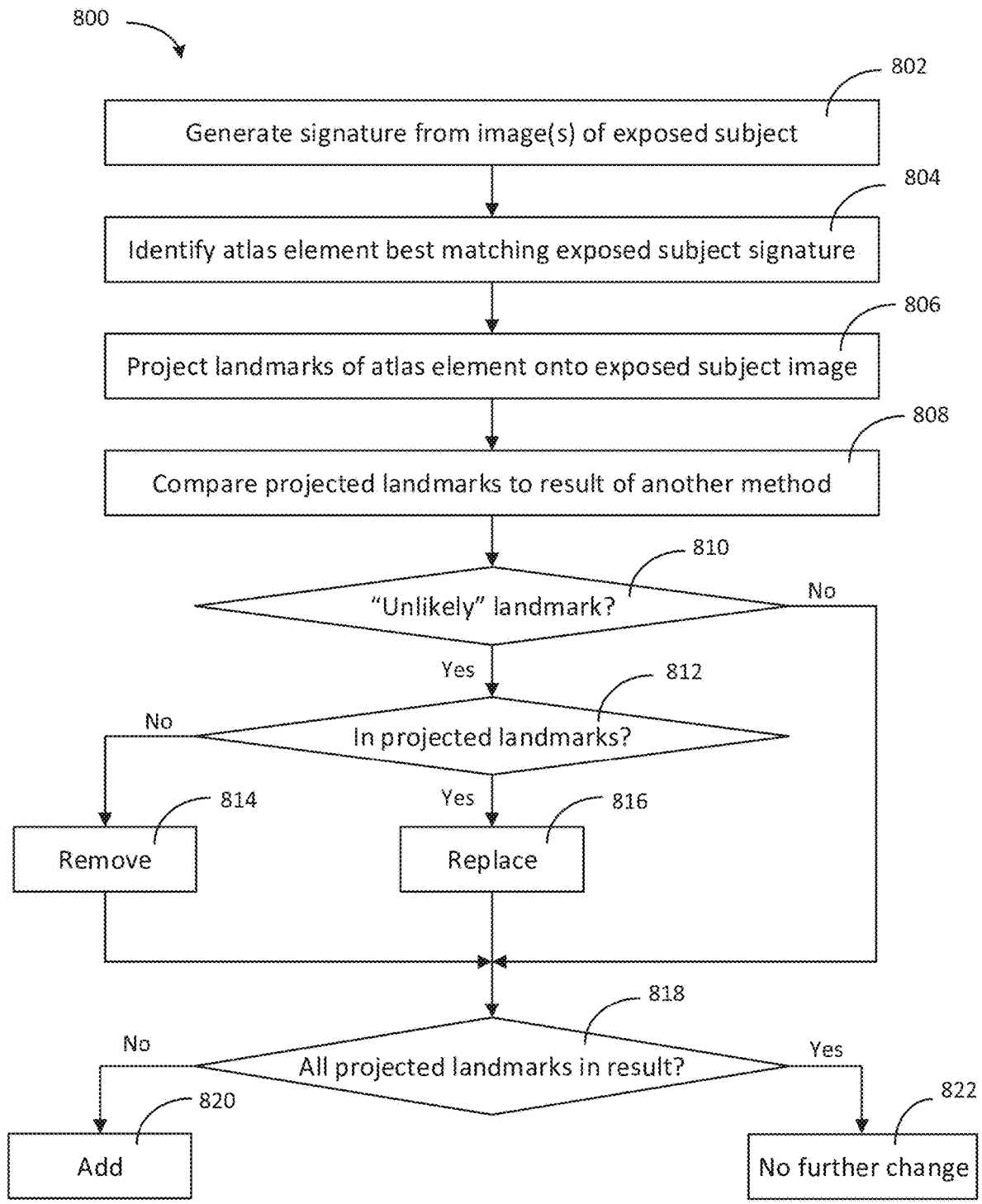
FIG. 8 is a flow chart of a method for identifying anatomical regions, in accordance with an exemplary embodiment.

Referring to FIG. 8, a flow chart 800 of a method for identifying anatomical regions is shown, in accordance with an exemplary embodiment. The method can be executed by the first anatomical region detector 130 in FIG. 1 and the first anatomical region detector 400 in FIG. 4. At an operation 802, a signature is computed for an exposed subject from one or more images of the exposed subject. As discussed above, the signature includes patient specific metrics and does not rely upon the machine and/or protocol to acquire the image(s). In some embodiments, the signature includes a water equivalent diameter distribution calculated from the image(s) using the fast method as discussed above. In some embodiments, the water equivalent diameter distribution is generated using another appropriate method. For example, certain devices may give the information as metadata in the scout image(s). In some embodiments, the signature may further include age, sex, size, etc., of the exposed subject.

At an operation 804, a best matching atlas element is identified from an atlas, where a signature of the best matching atlas element matches the signature of the exposed subject the best. The atlas includes a group of images, each called an atlas element. Each atlas element includes image data, associated signature, and associated landmarks that have been annotated. In some embodiments, the difference between the signature of the exposed subject and the signature of each atlas element is calculated. The atlas element with the minimum difference is identified to be the best matching atlas element.

At an operation 806, landmarks of the best matching atlas element are projected onto an image of the exposed subject to create projected landmarks for the image. In some embodiments, the z-axis values of the landmarks are mapped onto corresponding z-axis positions of the image. In some embodiments, the projected landmarks can be used alone for anatomy localization—and operations 808 through 820 may not be needed. In some embodiments, the projected landmarks are used to correct the result of another anatomy localization method and at least some of operations 808 through 820 can be performed.

At an operation 808, the projected landmarks are compared to a second set of landmarks identified by the another method. In some embodiments, difference in z-axis values between a projected landmark and a corresponding landmark in the second set of landmarks is calculated. A confidence score is determined based on the difference. In some embodiments, the greater the difference, the lower the confidence score. In some embodiments, a first confidence score is given to the difference greater than a predefined threshold, and a second confidence score is given to the difference not greater than the predefined threshold, where the first confidence score is lower than the second confidence score. In some embodiments, if a landmark identified by the another method does not have a corresponding projected landmark, a special confidence score is given to indicate so.

At an operation 810, it is determined whether any landmark identified by the second method is "unlikely" to be correct based on the comparison. In some embodiment, a confidence score associated with each landmark of the second method is compared with a predefined threshold score. If the confidence score is lower than the threshold score, the associated landmark identified by the second method is determined "unlikely" to be correct. If the confidence score is not lower than the threshold score, the associated landmark identified by the second method is not labeled as "unlikely." If it is determined at operation 810 that no landmark in the result of the second method is "unlikely," the method proceeds to an operation 818, which will be discussed later below.

If it is determined at operation 810 that a particular landmark in the second set of landmarks is "unlikely," then at an operation 812, it is determined whether that particular landmark has a corresponding projected landmark. For example, the another method may have identified a landmark that marks the end of the pelvis and the start of the lower limb while the projected landmarks do not include a corresponding landmark. If this is the case, the particular landmark is removed from the second set of landmarks, at an operation 814.

If it is determined at operation 812 that the "unlikely" landmark has a counterpart in the projected landmarks, then at an operation 816, the "unlikely" landmark is replaced by the corresponding one in the projected landmarks. For example, the second method has identified a landmark that marks the end of the pelvis and the start of the lower limb. However, the z-axis value of the landmark is substantially different from the z-axis value of the corresponding projected landmark. This particular landmark in second set of landmarks can be replaced by the corresponding projected landmark, at an operation 816.

In some embodiments, the method 800 may further include an operation 818, where it is determined whether all projected landmarks are in the second set of landmarks identified by the another anatomy localization method. For example, the projected landmarks may include a landmark that mark the end of the pelvis and the start of the lower limb while the second set of landmarks do not include a counterpart. The missing landmark can be added to the second set of landmarks, at an operation 820. If it is determined at operation 818 that all projected landmarks have a corresponding one in the second set of landmarks, then at operation 822, no further change is made to the result.

It should be understood that the process as shown in FIG. 8 is for illustration not for limitation. An appropriate process may include more, fewer, or different operations than those shown in FIG. 8.

The method as disclosed herein has been tested in conjunction with an existing anatomical region detection method implemented in GE DoseWatch®. False positives generated by DoseWatch® were removed.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

What is claimed is:

1. A method for automatically identifying anatomical regions in medical images, the method comprising:
   generating a water equivalent diameter distribution of an exposed subject from one or more images of the exposed subject;
   identifying a best matching atlas element from an atlas based on the water equivalent diameter distribution, wherein the atlas includes a group of atlas elements, each atlas element includes landmarks associated with a set of image data and a water equivalent diameter distribution associated the set of image data, the water equivalent diameter distribution of the best matching atlas element matches the water equivalent diameter distribution of the exposed subject the best among the atlas; and projecting landmarks of the best matching atlas element onto an image of the exposed subject to generate projected landmarks for the image of the exposed subject.

2. The method of claim 1, wherein generating the water equivalent diameter distribution of the exposed subject comprises:
   calculating water equivalent diameters for a set of slice images of the exposed subject;
   calibrating a scout image of the exposed subject using the calculated water equivalent diameters; and
   calculating the water equivalent diameter distribution along a longitudinal axis of the scout image based on the calibration.

3. The method of claim 1, further comprising comparing at least one of age, sex, and size of the exposed subject with those of the group of atlas elements.

4. The method of claim 1, wherein identifying the best matching atlas element comprises:
   comparing the water equivalent diameter distribution of the exposed subject to the water equivalent diameter distribution of each atlas element in the atlas; and
   identifying an atlas element with the minimum difference as the best matching atlas element.

5. The method of claim 1, further comprising:
   comparing the projected landmarks to a result of a different anatomy localization method, wherein the result includes a second set of landmarks identified by the different anatomy localization method; and
   correcting the result based on the comparison.

6. The method of claim 5, wherein comparing the projected landmarks to the result comprises:
   determining a confidence score associated with each landmark of the second set of landmarks based on a difference between the associated landmark and a corresponding landmark in the projected landmarks; and
   determining that a particular landmark in the second set of landmarks is unlikely to be correct based on the associated confidence score;
   wherein correcting the result comprises correcting the particular landmark determined unlikely to be correct.

7. The method of claim 6, further comprising determining whether the projected landmarks include a landmark corresponding to the particular landmark, wherein correcting the particular landmark determined unlikely to be correct comprises:
   in response to determining that no corresponding landmark is included in the projected landmarks, removing the particular landmark from the result of the different anatomy localization method; and
   in response to determining that the corresponding landmark is included in the projected landmarks, replacing the particular landmark in the result with the corresponding landmark.

8. The method of claim 5, wherein comparing the projected landmarks to the results comprises determining that a particular landmark in the projected landmarks does not have a corresponding landmark in the result, and correcting the result based on the comparison comprises adding the particular landmark to the result.

9. A processing system for automatically identifying anatomical regions in medical images, the processing system comprising:
   a signature generator configured to generate a water equivalent diameter distribution of an exposed subject from one or more images of the exposed subject;
   a signature matcher configured to identify a best matching atlas element from an atlas based on the water equivalent diameter distribution, wherein the atlas includes a group of atlas elements, each atlas element includes landmarks associated with a set of image data and a water equivalent diameter distribution associated the set of image data, the water equivalent diameter distribution of the best matching atlas element matches the water equivalent diameter distribution of the exposed subject the best among the atlas; and
   a landmark projector configured to project landmarks of the best matching atlas element onto an image of the exposed subject to generate projected landmarks for the image of the exposed subject.

10. The processing system of claim 9, wherein the signature generator is further configured to:
    calculate water equivalent diameters for a set of slice images of the exposed subject;
    calibrate a scout image of the exposed subject using the calculated water equivalent diameters; and
    calculate the water equivalent diameter distribution along a longitudinal axis of the scout image based on the calibration.

11. The processing system of claim 9, wherein the signature matcher is further configured to compare at least one of age, sex, and size of the exposed subject with those of the group of atlas elements.

12. The processing system of claim 9, wherein the signature matcher is further configured to:
    compare the water equivalent diameter distribution of the exposed subject to the water equivalent diameter distribution of each atlas element in the atlas; and
    identify an atlas element with the minimum difference as the best matching atlas element.

13. The processing system of claim 9, further comprising:
    a result comparator configured to compare the projected landmarks to a result of a different anatomy localization method, wherein the result includes a second set of landmarks identified by the different anatomy localization method; and
    a result corrector configured to correct the result based on the comparison.

14. The processing system of claim 13, wherein the result comparator is further configured to:
    determine a confidence score associated with each landmark of the second set of landmarks based on a difference between the associated landmark and a corresponding landmark in the projected landmarks; and
    determine that a particular landmark in the second set of landmarks is unlikely to be correct based on the associated confidence score; and
    the result corrector is further configured to correct the particular landmark determined unlikely to be correct.

15. The processing system of claim 14, wherein the result comparator is further configured to determine whether the projected landmarks include a landmark corresponding to the particular landmark, the result corrector is further configured to:
    in response to determining that no corresponding landmark is included in the projected landmarks, remove the particular landmark from the result of the different anatomy localization method; and
    in response to determining that the corresponding landmark is included in the projected landmarks, replace the particular landmark in the result with the corresponding landmark.

16. The processing system of claim 13, wherein the result comparator is further configured to determine that a particular landmark in the projected landmarks does not have a corresponding landmark in the result, and the result corrector is further configured to add the particular landmark to the result.

17. A non-transitory computer readable medium comprising instructions which, when executed by a processing system, cause the processing system to perform operations comprising:

generating a water equivalent diameter distribution of an exposed subject from one or more images of the exposed subject;

identifying a best matching atlas element from an atlas based on the water equivalent diameter distribution, wherein the atlas includes a group of atlas elements, each atlas element includes landmarks associated with a set of image data and a water equivalent diameter distribution associated the set of image data, the water equivalent diameter of the best matching atlas element matches the water equivalent diameter of the exposed subject the best among the atlas; and projecting landmarks of the best matching atlas element onto an image of the exposed subject to generate projected landmarks for the image of the exposed subject.

18. The non-transitory computer readable medium of claim 17, wherein the operation of generating the water equivalent diameter distribution of the exposed subject comprises:

calculating water equivalent diameters for a set of slice images of the exposed subject;

calibrating a scout image of the exposed subject using the calculated water equivalent diameters; and calculating the water equivalent diameter distribution along a longitudinal axis of the scout image based on the calibration.

19. The non-transitory computer readable medium of claim 17, wherein the operations further comprise:

comparing the projected landmarks to a result of a different anatomy localization method, wherein the result includes a second set of landmarks identified by the different anatomy localization method;

determining that a particular landmark in the second set of landmarks is unlikely to be correct based on the comparison;

determining whether the projected landmarks include a landmark corresponding to the particular landmark;

in response to determining that no corresponding landmark is included in the projected landmarks, removing the particular landmark from the result of the different anatomy localization method; and in response to determining that the corresponding landmark is included in the projected landmarks, replacing the particular landmark in the result with the corresponding landmark.

20. The non-transitory computer readable medium of claim 17, wherein the operations further comprise:

comparing the projected landmarks to a result of a different anatomy localization method, wherein the result includes a second set of landmarks identified by the different anatomy localization method;

determining that a particular landmark in the projected landmarks does not have a corresponding landmark in the result; and adding the particular landmark to the result.

* * * * *